(12) United States Patent
Kasai et al.

(10) Patent No.: US 7,795,588 B2
(45) Date of Patent: Sep. 14, 2010

(54) INSPECTION APPARATUS

(75) Inventors: Shintaro Kasai, Tokyo (JP); Takeaki Itsuji, Hiratsuka (JP); Toshihiko Ouchi, Sagamihara (JP)

(73) Assignee: Canon Kabushiki Kaisha, Tokyo (JP)

( * ) Notice: Subject to any disclaimer, the term of this patent is extended or adjusted under 35 U.S.C. 154(b) by 307 days.

(21) Appl. No.: 12/046,907

(22) Filed: Mar. 12, 2008

(65) Prior Publication Data
US 2008/0224071 A1 Sep. 18, 2008

(30) Foreign Application Priority Data
Mar. 13, 2007 (JP) ............................. 2007-063613

(51) Int. Cl.
G01J 5/02 (2006.01)
(52) U.S. Cl. ............... 250/341.1; 250/492.1; 250/340; 250/343; 250/338.1; 250/339.06
(58) Field of Classification Search ............. 250/492.1, 250/340, 343, 338.1, 338.5, 339.06, 341.1
See application file for complete search history.

(56) References Cited

U.S. PATENT DOCUMENTS

| | | | |
|---|---|---|---|
| 5,850,408 A | 12/1998 | Ouchi et al. | 372/27 |
| 6,055,251 A | 4/2000 | Ouchi et al. | 372/28 |
| 6,222,868 B1 | 4/2001 | Ouchi et al. | 372/50 |
| 7,564,034 B2 * | 7/2009 | Ouchi | 250/340 |
| 2005/0233490 A1 | 10/2005 | Kasai et al. | 438/46 |
| 2006/0197021 A1 * | 9/2006 | Ouchi | 250/343 |
| 2007/0070358 A1 | 3/2007 | Ouchi | 356/614 |
| 2007/0148047 A1 * | 6/2007 | Itsuji et al. | 422/82.11 |
| 2007/0218376 A1 | 9/2007 | Ouchi | 430/56 |
| 2007/0267575 A1 * | 11/2007 | Holly et al. | 250/343 |
| 2009/0219511 A1 * | 9/2009 | Itsuji | 356/51 |

OTHER PUBLICATIONS

Nagel, et al "A functionalized THz sensor for Marker-free DNA analysis" Phys. Med. Bio., 48 (2003) pp. 3625-3636.*
Nagel, et al "Integrated planar terahertz resonator for femtomolar sensitivity label-free detection of DNA hybridization" Applied Optics, vol. 41, No. 10, pp. 2074-2078 (Apr. 1, 2002).*
Nagel, M. et al., "A functionalized THz sensor for Marker-free DNA analysis", Institute of Physics Publishing, Phys. Med. Bio., 48 (2003), pp. 3625-3636.
Nagel, M. et al., "Integrated planar terahertz resonators for femtomolar sensitivity label-free detection of DNA hybridization", Applied Optics, vol. 41, No. 10, pp. 2074-2078 (Apr. 1, 2002).

* cited by examiner

Primary Examiner—Robert Kim
Assistant Examiner—Michael Maskell
(74) Attorney, Agent, or Firm—Fitzpatrick, Cella, Harper & Scinto (57) ABSTRACT

The invention is to provide an inspection apparatus causing interactions of plural times between an object and an electromagnetic wave, thereby enabling inspection with a satisfactory sensitivity even for an object of a trace amount. The inspection apparatus detects information from an object 112 based on a change in an electromagnetic wave transmission state caused by plural times of interactions between the electromagnetic wave and the object 112. The inspection apparatus includes a transmission line 16, an electromagnetic wave supplying and detecting unit 111 for supplying the transmission line 16 with the electromagnetic wave and detecting the electromagnetic wave, a reflection unit 110 for reflecting the electromagnetic wave transmitting through the transmission line 16, and an inspection unit 113 for placing the object 112 between the electromagnetic wave supplying and detecting unit 111 and the reflection unit 110, wherein the transmission line 16, the reflection unit 110 and the inspection unit 113 are formed on a same substrate 11.

6 Claims, 10 Drawing Sheets

FIG. 1A

PLAN VIEW

FIG. 1B

SECTIONAL VIEW ALONG SIGNAL LINE 15

TERAHERTZ WAVEFORM IN SIMULATION

FIG. 5A

PLAN VIEW

FIG. 5B

SECTIONAL VIEW ALONG TRANSMISSION PATH 51c

FIG. 6A

PLAN VIEW

FIG. 6B

SECTIONAL VIEW ALONG SIGNAL LINE 65

FIG. 7

TERAHERTZ WAVEFORM IN SIMULATION

FIG. 8A

PLAN VIEW

FIG. 8B

SECTIONAL VIEW ALONG SIGNAL LINE 85

FIG. 9A

PLAN VIEW

FIG. 9B

SECTIONAL VIEW ALONG LINE 9B-9B

FIG. 10

INSPECTION APPARATUS

BACKGROUND OF THE INVENTION

1. Field of the Invention

The present invention relates to an inspection apparatus for detecting, by an electromagnetic wave, information (physical properties, identity, concentration, presence/absence and the like) of a specimen (object of inspection), and more particularly to an inspection apparatus for detecting the information of the object, utilizing an electromagnetic wave of an arbitrary frequency region of from 30 GHz to 30 THz (referred to herein as terahertz wave).

2. Description of the Related Art

Technical developments utilizing terahertz wave are actively done recently. In particular, the photon energy of the terahertz wave is comparable to the energy of molecular skeletal vibration or intermolecular interaction, and the technology utilizing the terahertz wave is used for analyses of substances for example by a spectrum obtained by a spectroscopic method.

Based on such situation, proposed is a construction for the purpose of detection or analysis of an object of a trace amount, in which a terahertz wave generating unit, a terahertz wave transmission unit, a terahertz wave detection unit and a sensor unit for so disposing an object as to cause an interaction with the terahertz wave are prepared on a same substrate (see Non-patent Document 1).

More specifically, a low-temperature grown gallium arsenide epitaxial layer is transferred for example onto a silicon substrate coated with a dielectric film, and a microstrip line-type transmission line is formed for example by a photolithographic technology. The low-temperature grown gallium arsenide epitaxial layer is provided thereon with two electrodes spaced by a gap of several micrometers to several tens of micrometers, thereby being utilized as a terahertz wave generating unit. A terahertz wave is generated by applying a voltage between the two electrodes and irradiating the gap with an ultra-short pulsed laser beam for example emitted by a mode-locked titanium sapphire laser. The generated terahertz wave is transmitted through the microstrip line type transmission line, and, after an interaction with the object disposed on the transmission line, is detected by a detector of a structure same as that of the terahertz wave generating unit.

In the construction above, the properties, identity, concentration, presence/absence and the like of the object are detected for example by observing the waveform of the terahertz wave transmitting through the microstrip line type transmission line and comparing the change between before and after the object is disposed.

On the other hand, proposed also is a construction, similar to the structure disclosed in Non-patent Document 1 but improved in the detection sensitivity by providing a ringed resonator on the microstrip line type transmission line (see Non-patent Document 2). The construction of Non-patent Document 2 similarly detects the properties, identity, concentration, presence/absence and the like of a substance contained in a liquid object, by determining for example the dielectric constant of the liquid object.

[Non-patent Document 1] Physics in Medicine and Biology, 48(2003), 3625

[Non-patent Document 2] Applied Optics, Vol. 41, No. 10, 2002, pp. 2074

SUMMARY OF THE INVENTION

When an object is disposed on a transmission line, the electromagnetic wave transmitting on the transmission line is subjected to an absorption in intensity or a delay in phase, by the object. However, when the absorption is very weak, it is difficult to precisely observe the change in the intensity of the electromagnetic wave between before and after the object is disposed. Also when the amount of delay in phase is very small, it is difficult to precisely observe the change in the phase of the electromagnetic wave between before and after the object is disposed.

In the method of Non-patent Document 1, the electromagnetic wave transmitting on the transmission line and transmitted by the object only once is detected. Therefore, the length of interaction of the electromagnetic wave and the object is approximately equal to the length of overlapping of the object with the transmission line. Consequently, in the case that the interaction of the electromagnetic wave and the object is not sufficiently strong, it is difficult to obtain the information of the object in precise manner.

On the other hand, in the method of Non-patent Document 2, it is difficult to utilize the electromagnetic wave over a wide frequency range because of the resonator type construction. Therefore, this method is suitable for a case where the frequency range containing the characteristic absorption of the object is known in advance to a certain extent and where such frequency range matches the resonance frequency of the resonator. However, detection of high sensitivity cannot necessarily be achieved in a situation where the frequency range containing the characteristic absorptions of various objects is difficult to match the resonance frequency of the resonator.

Thus, in the inspection apparatus of transmission line type, an improvement in the detection sensitivity is being desired.

In view of the above-described problems, the inspection apparatus of the present invention, for inspecting information of an object based on a change in an electromagnetic wave transmission state caused by plural times of interactions between the electromagnetic wave and the object, including a transmission line, an electromagnetic wave supplying and detecting unit for supplying and detecting the electromagnetic wave, a reflection unit for reflecting the electromagnetic wave transmitting through the transmission line, and an inspection unit for placing the object between the electromagnetic wave supplying and detecting unit and the reflection unit, wherein the transmission line, the reflection unit and the inspection unit are formed on a same substrate.

The aforementioned construction of the present invention enables, utilizing a reflected wave in the reflection unit of the electromagnetic wave transmitting through the transmission line, to cause interactions of plural times between the object and the electromagnetic wave, thereby achieving a highly sensitive detection even on the object of a small amount.

Further features of the present invention will become apparent from the following description of exemplary embodiments with Document to the attached drawings.

DESCRIPTION OF THE EMBODIMENTS

In the following, the present invention will be described by the working principle thereof and by exemplary embodiment in which the present invention is applicable. The inspection apparatus of the present invention includes, in an exemplary embodiment thereof, a transmission line for transmitting an electromagnetic wave, an electromagnetic wave supplying and detecting unit for supplying the transmission line with the electromagnetic wave and receiving and detecting the electromagnetic wave from the transmission line, a reflection unit for reflecting the electromagnetic wave and returning it to the transmission line, and an inspection unit for placing the object. In addition, a coupling unit for coupling the electromagnetic wave with the transmission line may be provided.

The inspection unit is provided between the electromagnetic wave supplying and detecting unit and the reflection unit, or, in the case that the coupling unit is provided, between such coupling unit and the reflection unit. The inspection unit may be so constructed as to place the object in a position containing at least a part of the range covered by the electric field distribution of the electromagnetic wave transmitting through the transmission line. The range covered by the electric field distribution means a range in which an electric field, equal to or larger than $1/e^2$ of the electric field of the electromagnetic wave transmitting through the transmission line, is present. In summary, the inspect unit places the object within a region where the electromagnetic wave transmitting in the transmission line toward the reflection unit and the electromagnetic wave transmitted in a direction farther away from the reflection unit are present mixedly, and in a position containing at least a part of the range covered by the electric field distribution. The electromagnetic wave is representatively a terahertz wave, and has a frequency within a range of from 30 GHz to 30 THz.

The transmission line, the inspection unit, the reflection unit and the coupling unit can be formed and integrated on a same substrate. In the case that the electromagnetic wave supplying and detecting unit includes a supplying unit for supplying the electromagnetic wave and a detecting unit for detecting the electromagnetic wave and that the supplying unit and the detecting unit are formed adjacent to each other in a continuous and common same layered structure, the electromagnetic wave supplying and detecting unit is also suitable for integration. Therefore, the electromagnetic wave supplying and detecting unit can also be formed and integrated on the same substrate. The continuous and common same layered structure is for example a low temperature-grown gallium arsenide film for a photoconductive switch structure to be described later.

The transmission line may have a structure including a dielectric unit and an electroconductive unit disposed at one or more portions of the dielectric unit. More specific examples of the transmission line include a microstrip line type transmission line, a strip line type transmission line, a suspended microstrip line type transmission line, a coplanar waveguide type transmission line, a grounded coplanar waveguide type transmission line, a slot line type transmission line, a microcoplanar strip line type transmission line, a coplanar strip line type transmission line, and a single path type transmission line.

The reflection unit is formed for example by discontinuously varying the impedance of the transmission line. More specifically, the reflection unit is constituted of a portion of an impedance mismatch, for example by a discontinuity or a change in width of the electoconductive unit or the dielectric unit, a discontinuity of a signal line, a change in width of the signal line, a bend in the signal line, a discontinuity in a ground electrode, a change in the dielectric constant in a dielectric layer (by employing a different material while maintaining the shape unchanged), a change in the thickness of the dielectric layer, or a change in the structure of transmission line (type of transmission line).

In such construction, the terahertz wave generated from the electromagnetic wave supplying and detecting unit is transmitted through the transmission line via the coupling unit, then causes an interaction with the object disposed on the transmission line, and reaches the reflection unit. The terahertz wave reflected by the reflection unit and returning by transmitting along the transmission line in the opposite direction again causes an interaction with the object, and reaches the electromagnetic wave supplying and detecting unit via the coupling unit. The object is inspected by detecting the terahertz wave that has caused interaction plural times (typically twice) with the object. The terahertz wave, interacting with the object before and after the reflection in the reflection unit, causes, as a result, a strong interaction with the object even in case of a trace amount, whereby the change in the transmission state of the terahertz wave, caused by presence/absence of the object or of a component therein, can be obtained from the detecting unit to obtain information on the presence/absence of the object or of the component therein.

Figure 1A:
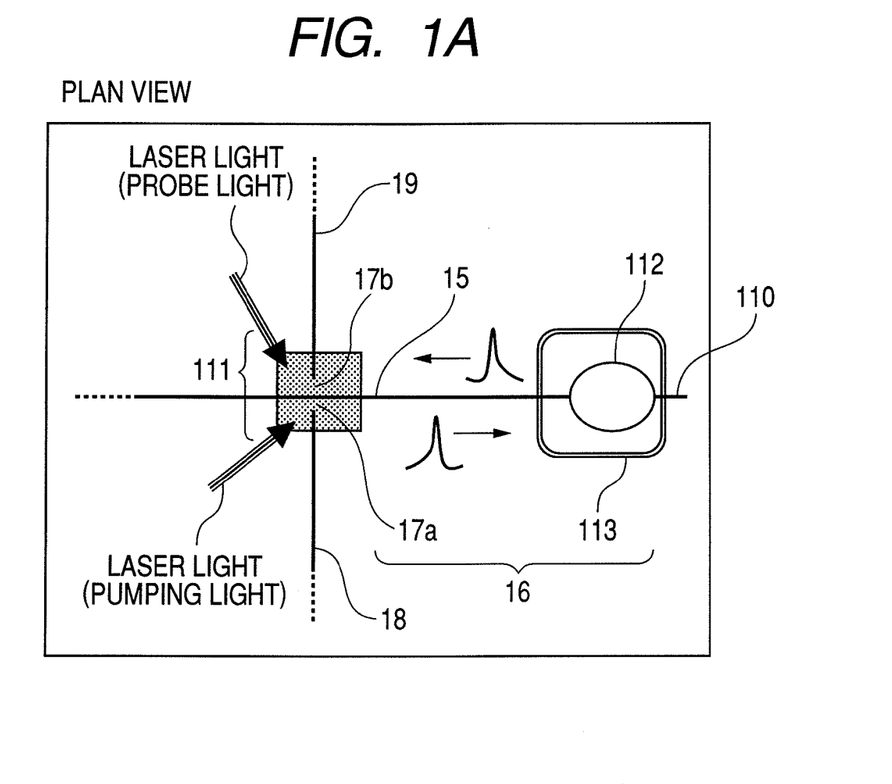
FIGS. 1A and 1B are schematic views illustrating an inspection apparatus of an exemplary embodiment and a first example of the present invention.
Figure 1B:
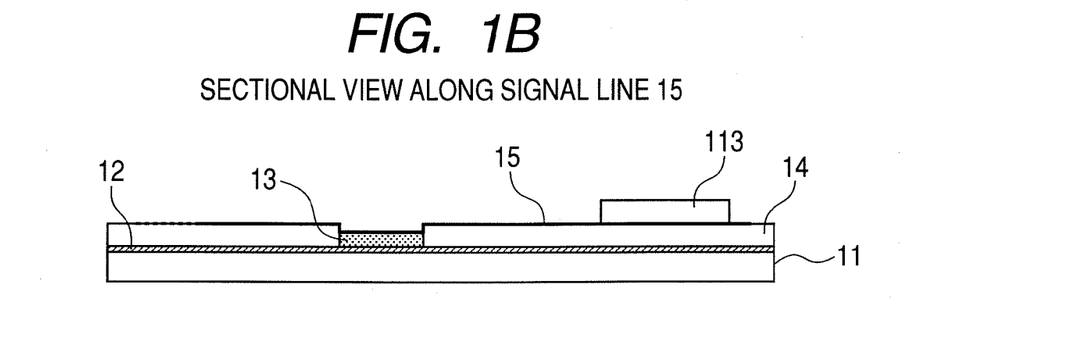

Now reference is made to FIGS. 1A and 1B for describing an exemplary embodiment more specifically. FIG. 1A is a plan view of an inspection apparatus, and FIG. 1B is a cross-sectional view of a signal line. In the inspection apparatus of the exemplary embodiment illustrated in FIGS. 1A and 1B, a metal surface (for example a metal surface formed by laminating titanium and gold respectively by 500 Å and 3000 Å by evaporation) formed for example by an evaporation on a substrate 11 (such as a silicon substrate) constitutes a ground electrode 12 for the transmission line. On the ground electrode 12, a low temperature-grown gallium arsenide film 13 is formed in a position for example by an epitaxial lift-off process, and a dielectric layer 14 that is relatively transparent to the terahertz wave (for example of benzocyclobutene) is formed thereon. The dielectric layer 14 has a thickness for example of 5 μm. The dielectric layer 14 is partially removed for example by a reactive ion etching to expose a part of the low temperature-grown gallium arsenide film 13. The low temperature-grown gallium arsenide film 13 for example has a square shape with a side of 2 mm.

On the dielectric layer 14, disposed is a metal signal line 15 having a width of about from 5 to 10 μm and a length of about 1 mm. The signal line 15 is constituted of a metal surface, formed by evaporating and laminating titanium and gold respectively by 500 Å and 3000 Å. The ground electrode 12, the dielectric layer 14 and the signal line 15 constitute a microstrip line type transmission line (transmission line) 16. On the low temperature-grown gallium arsenide film 13, a bias voltage supplying line 18 and a signal reading line 19 are provided with gaps 17a, 17b of about 5 to 10 μm to the signal line 15. The signal line 15 is discontinued at a terminal end thereof, where the impedance changes discontinuously. The discontinued terminal end of the signal line 15 constitutes a reflection unit 110. The bias voltage supplying line 18 and the signal reading line 19 can also be formed by an evaporation process.

A terahertz wave is generated by applying a voltage of about 10 V from the bias voltage supplying line 18 and by irradiating the gap 17a with an ultra short pulsed laser light emitted for example from a mode locked titanium sapphire laser. This portion constitutes the supplying unit of the electromagnetic wave supplying and detecting unit 111. The signal reading line 19 is connected to a signal amplifier (not illustrated). The terahertz wave is detected by irradiating the gap 17b also with an ultra short pulsed laser light emitted for example from a mode locked titanium sapphire laser. This portion constitutes the detecting unit of the electromagnetic wave supplying and detecting unit 111. The electromagnetic wave supplying and detecting unit 111 is constituted of the low temperature-grown gallium arsenide film 13, the signal line 15, the gaps 17a, 17b, the bias voltage supplying line 18 and the signal reading line 19, which are in a continuous and common same layered structure.

In the present exemplary embodiment, a portion where the gaps 17a, 17b, the bias voltage supplying line 18, the signal reading line 19 and the signal line 15 are gathered constitutes the electromagnetic wave supplying and detecting unit 111 and serves the coupling unit to the microstrip line type transmission line 16. The coupling unit in this case is not particularly provided for this purpose. The supplying unit and the detecting unit of the electromagnetic wave supplying and detecting unit 111 are formed adjacent to each other, in a structure containing a continuous and common same layer of the low temperature-grown gallium arsenide film 13 for the photoconductive switch structure.

In the above-described construction, the terahertz wave generated from the supplying unit of the electromagnetic wave supplying and detecting unit 111 is transmitted through the transmission line 16, then reflected by the reflection unit 110, then is transmitted in the opposite direction along the transmission line 16 and detected by the detecting unit of the electromagnetic wave supplying and detecting unit 111. The electromagnetic wave supplying and detecting unit 111 can detect the terahertz wave immediately after the generation and the terahertz wave returned by the reflection in the reflection unit 110.

The signal line 15 is so constructed that the object 112 can be placed thereon. More specifically, in the present exemplary embodiment, a liquid reservoir 113 for holding the object is provided as the inspection unit, in a region over the signal line 15 and between the reflection unit 110 and the electromagnetic wave supplying and detecting unit 111 (or the coupling unit). In FIG. 1A, the object 112 is illustrated as to be held in a partial area of the liquid reservoir 113, but in practice, the object 112 often spreads to the entire area of the liquid reservoir 113. The liquid reservoir 113 is prepared for example with a resin. The liquid reservoir of a resinous material is prepared for example by a photolithographic process utilizing a photosensitive epoxy resin. In the present case, the liquid reservoir 113 is formed by preparing a closed area with a barrier-like structure of a resin.

The object may be placed on the signal line 15 even without the liquid reservoir 113. Thus, the surface of the transmission line 16 may be utilized as the inspection unit. The inspection area may be constituted by an entire area which is positioned between the reflection unit 110 and the electromagnetic wave supplying and detecting unit 111 and on the signal line 15, and which is covered by the electric field distribution of the transmitting terahertz wave.

Figure 2:
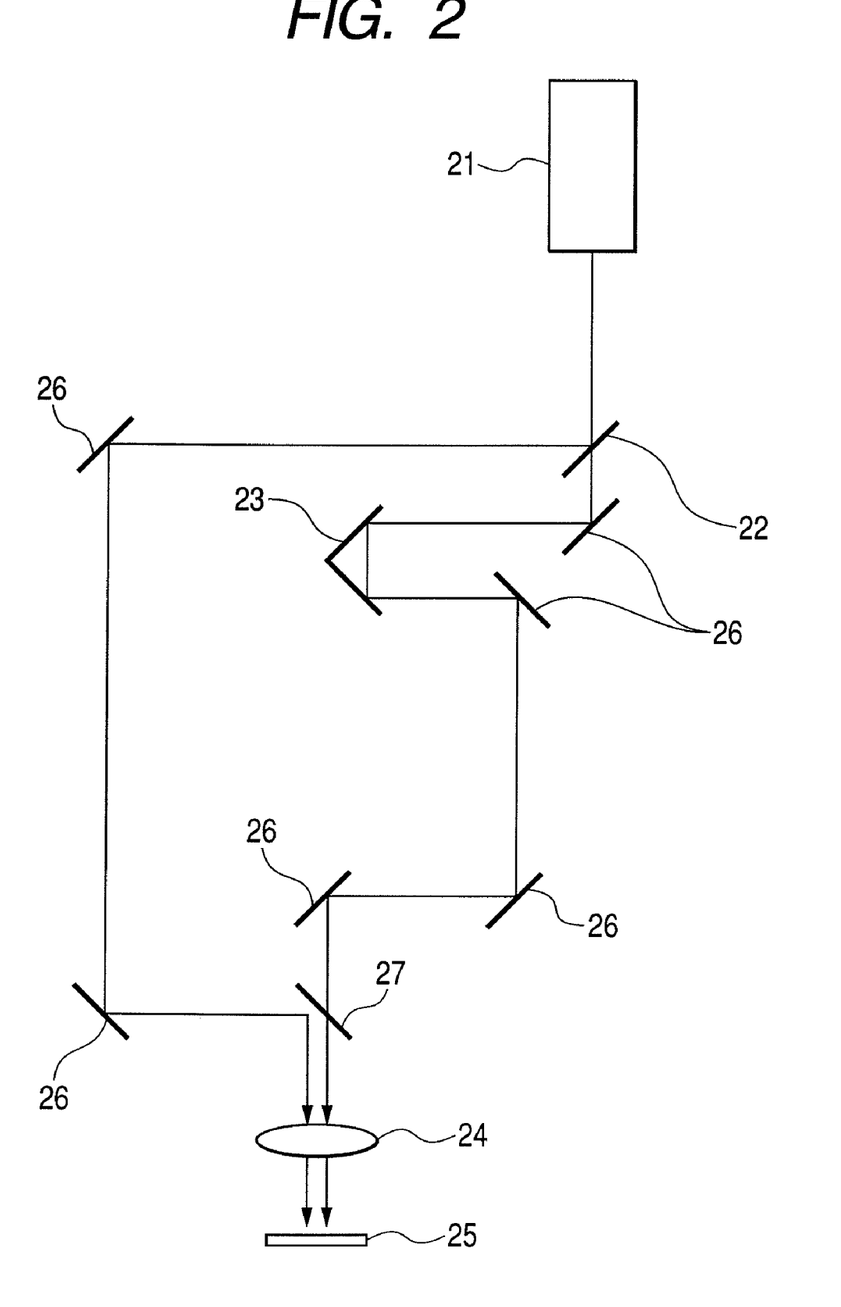
FIG. 2 is a view illustrating an example of a peripheral optical system employed in the inspection apparatus.

FIG. 2 illustrates a peripheral optical system required for the above-described inspection apparatus. As illustrated in FIG. 2, an ultra short pulsed laser light emitted from a mode-locked titanium sapphire laser 21 is split by a beam splitter 22. One of the lights passes through a totally reflecting mirror 26 and a half mirror 27 and is focused on the gap 17a (voltage application side) of the supplying unit illustrated in FIGS. 1A and 1B. The other of the femtosecond laser lights split by the beam splitter 22 passes through a delaying optical system 23, a totally reflecting mirror 26 and a half mirror 27, and is focused on the gap 17b (side connected to the signal amplifier) of the detecting unit illustrated in FIGS. 1A and 1B.

In this construction, the gap 17a and the gap 17b are positioned very close (separated for example 10 μm that is about the width of the signal line 15). Therefore, the split laser lights may be re-united before being focused, and may be focused on the respective gaps by a single objective lens 24.

When the optical path length of the laser light focused on the gap 17a (pumping light) is made equal to the optical path length of the laser light focused on the gap 17b (probe light), by extending or contracting the delaying optical system 23, the terahertz wave immediately after generation can be observed. Also by regulating the position of the delaying optical system 23 in such a manner that the optical path length is somewhat longer (in this case by about 1 mm to several mm) in the probe light than in the pumping light, the terahertz wave returned by the reflection in the reflection unit 110 can be observed by the detecting unit of the electromagnetic wave supplying and detecting unit 111.

Figure 3:
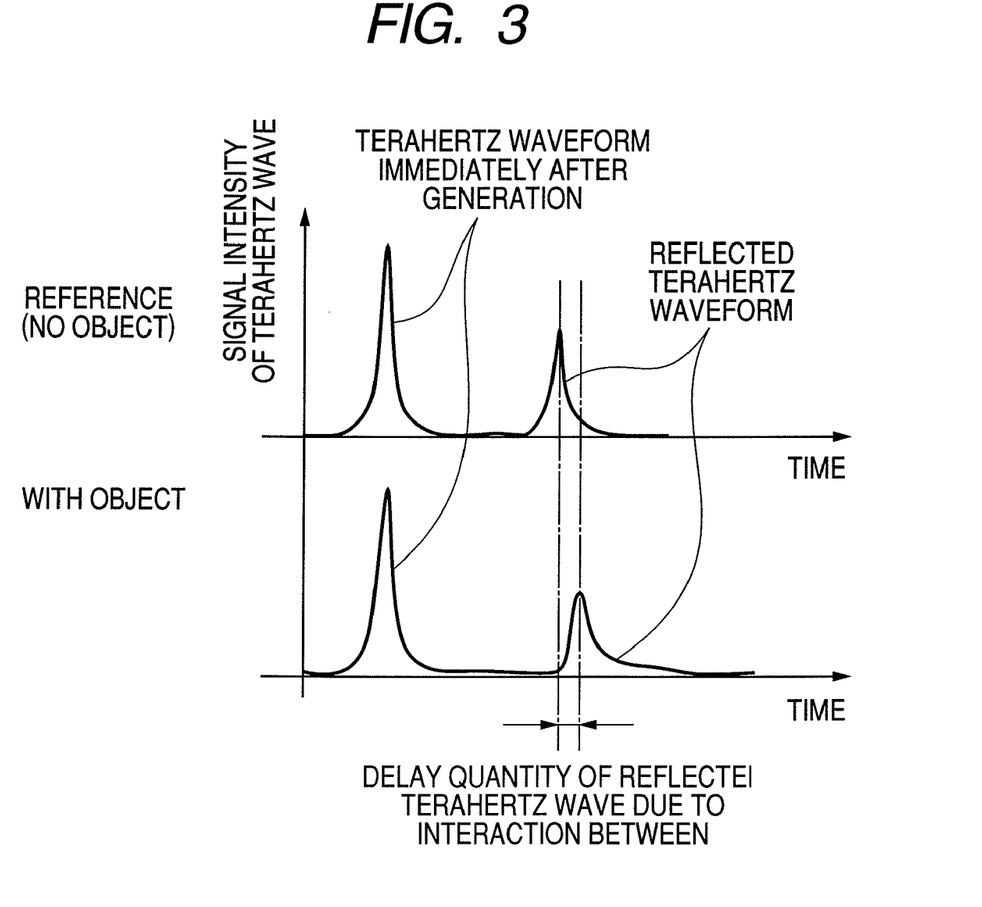
FIG. 3 is a schematic view illustrating a waveform of a terahertz wave as a function of time.

FIG. 3 is a schematic view illustrating a signal obtained with the inspection apparatus as described above. The upper and lower two graphs schematically indicate waveforms of the detected terahertz wave as a function of time. The upper graph is a waveform of the terahertz wave as a function of time, obtained in a measurement before the object 112 is placed on the signal line 15. The lower graph is a waveform of the terahertz wave as a function of time, obtained in a measurement after the object 112 is placed on the signal line 15. As shown in either graph, there are two peaks corresponding to the terahertz wave immediately after generation and the terahertz wave returned by the reflection in the reflection unit 110. The two peaks become different in the time difference or in the ratio thereof by the presence or absence of the object 112 on the signal line 15. This is because the terahertz wave causes an interaction with the object 112 on the signal line 15, thereby inducing a delay in time or an attenuation in the terahertz wave transmitting in the transmission line 16 and reaching the detecting unit.

The terahertz wave returned by the reflection in the reflection unit 110 has naturally to have an intensity of a level detectable by the electromagnetic wave supplying and detecting unit 111. More specifically, the electromagnetic wave reflected by the reflection unit 110 is required, upon reaching the electromagnetic wave supplying and detecting unit 111, to have an electromagnetic wave intensity equal to or higher than the electromagnetic wave detecting sensitivity. For this purpose, the intensity of the supplied electromagnetic wave, the reflectance of the reflection unit 110 and the transmission loss in the transmission line 16 are selected suitably.

Figure 4:
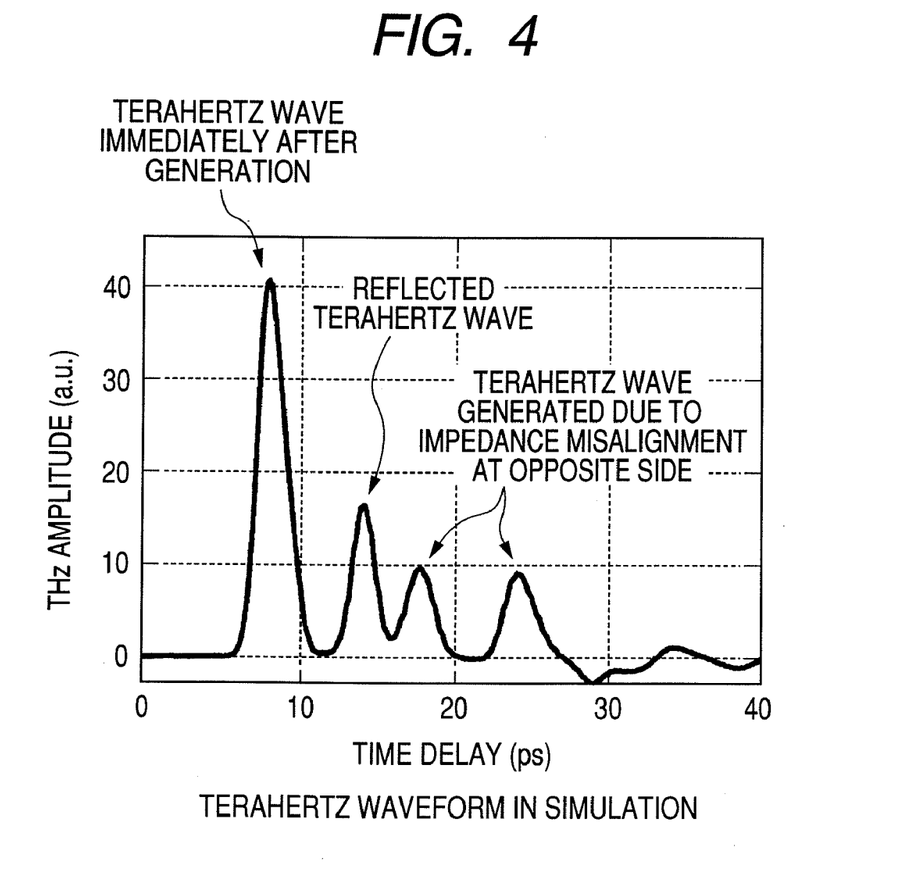
FIG. 4 is a schematic view illustrating a waveform of a terahertz wave as a function of time, obtained by a simulation.

A signal that was assumed to be obtained by such inspection apparatus was determined by a simulation. FIG. 4 illustrates the waveform of a terahertz wave obtained by the simulation. A first peak indicates a waveform of the terahertz wave immediately after generation. A second peak indicates a terahertz wave returned by reflection in the reflection unit 110. Third and subsequent peaks are terahertz waves reflected by an impedance mismatch, for example at the boundary between the dielectric layer 14 (formed by benzocyclobutene in the present case) and the low temperature-grown gallium arsenide film 13. In particular, these are terahertz waves reflected by such impedance mismatch portions after being transmitted in a direction opposite to the reflection unit 110.

In certain cases, there may be detected a waveform reflecting the result of interactions of three or more times between such terahertz wave reflected by the impedance mismatch portions and the object 112. For this purpose, a positional regulation corresponding to such waveform detection may be executed by the delaying optical system 23.

In the inspection apparatus of the above-described construction, the terahertz wave causes an interaction with the object 112 at least twice, in the forward path from generation to the reflection unit 110, and in the return path from the reflection to the electromagnetic wave supplying and detecting unit 111. Therefore, the measurement can be executed with a high sensitivity, even when the object 112 is present in a trace amount. Thus the information of the object can be obtained with a high sensitivity. Also the supplying unit and the detecting unit may be formed adjacent to each other in a portion of the electromagnetic wave supplying and detecting unit 111, whereby a major part of the inspection apparatus can be integrated on a single substrate and the apparatus can be made compact.

Figure 10:
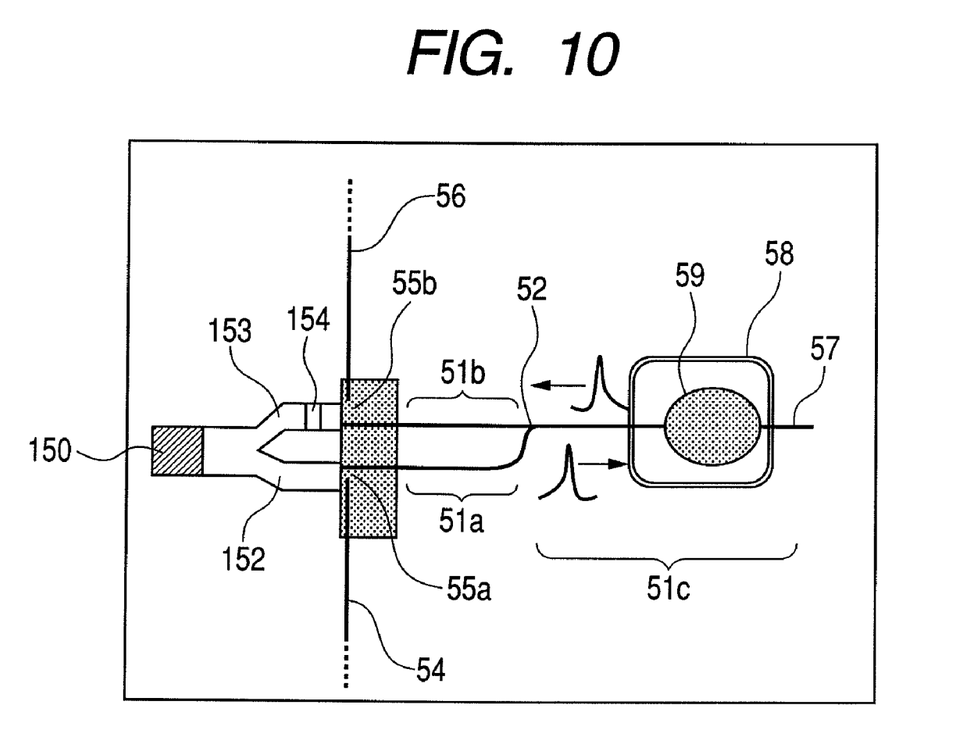
FIG. 10 is a schematic view of an inspection apparatus, in a variation of the second example of the present invention.

The pumping light and the probe light, irradiating the electromagnetic wave supplying and detecting unit 111, may execute irradiation in the following manner, instead of irradiation from above the gaps 17a, 17b by the optical system illustrated in FIG. 2. This will be described with reference to FIG. 10, illustrating a variation of a second example to be described later. In this example, for example a mode-locked semiconductor laser 150 is mounted on the substrate and generates a pulse of about 0.3 psec, which is coupled with the optical waveguide. One of the laser lights transmitting in the optical waveguide passes a branched optical waveguide 152 and irradiates a lateral face, corresponding to a gap 55a, of a low temperature-grown gallium arsenide film 53 constituting a photoconductive switch of the electromagnetic wave supplying and detecting unit. The other laser light transmitting in the optical waveguide passes another branched optical waveguide 153 and irradiates a lateral face, corresponding to a gap 55b, of the low temperature-grown gallium arsenide film 53 constituting the photoconductive switch of the electromagnetic wave supplying and detecting unit. A delaying device 154 is provided in the other branched optical waveguide 153, and, by changing the delay quantity thereof, the change in time of the electric field strength of the terahertz pulse transmitted through the transmission line and reading the gap 55b can be measured. The delaying device 154 may be constituted of a device which changes the refractive index of the optical waveguide by a voltage application. The optical waveguides 152, 153 may be formed, for example, by increasing the refractive index of the dielectric layer constituting the transmission line only in the corresponding portion by an exposure or the like. In this manner, the pumping light and the probe light may be irradiated, utilizing the branched optical waveguides, from the lateral faces of the low temperature-grown gallium arsenide film 53 on which the gaps 55a, 55b are formed. Such construction enables to easily form the electromagnetic wave supplying and detecting unit on the substrate, thereby enabling integration more easily.

In the following, the symbols in the drawings are summarized:

11, 91: substrate
12, 92a, 92b, 92c: transmission line (ground electrode)
13, 53, 93: electromagnetic wave supplying and detecting unit (low temperature-grown gallium arsenide film)
14, 94: transmission line (dielectric layer)
15, 65, 85, 95: transmission line (signal line)
16, 51, 61, 81: transmission line (microstrip line type transmission line)
17, 55, 68, 88: electromagnetic wave supplying and detecting unit (gap)
18, 54, 67, 87, 96: bias voltage supply line
19, 56, 69, 89, 97: signal reading line
23: delaying optical system
25: inspection apparatus of present invention
57, 63, 83, 110: reflection unit
58, 64, 84, 98, 113: inspection unit (liquid reservoir)
59, 112: object
62, 82, 111: electromagnetic wave supplying and detecting unit.

EXAMPLES

Based on the exemplary embodiment described above, more specific examples will be described in the following.

First Example

Now a first example will be described. In this example having a basic construction same as the above-described embodiment shown in FIGS. 1A and 1B, a pumping light of an intensity of 10 mW is focused on the gap 17a, while a probe light of an intensity of 5 mW is focused on the gap 17b. A voltage of 10 V is supplied to the bias supplying line 18, and the signal line 15 is maintained at a potential of 0 V.

In the present example, an aqueous DNA solution is dropped as an object 112 into the liquid reservoir 113, by a commercial micropipette or microinjector. The liquid reservoir 113 can be prepared in the form of a frame, by coating a photosensitive epoxy resin with a thickness of about 5 μm and removing the material of the interior, while leaving the material only in an edge portion. The dropped amount of the object 112 is for example about 100 nl. The DNA solution is an aqueous solution of a concentration of about 0.5 μg/μl.

The inspection of the object in the present example is executed in the following manner. At first a reference terahertz waveform, before the dropping of the object 112, is measured. In this operation, the pumping light is modulated, for example by an optical chopper, with a modulating frequency of about 1 kHz. The signal reading line 19 is connected to a high-gain amplifier, of which output is supplied to a lock-in amplifier to measure the terahertz wave reaching the electromagnetic wave supplying and detecting unit by a synchronized rectifying method.

Then an aqueous solution of double-strand DNA is dropped in the liquid reservoir 113, and, after sufficient drying, the terahertz wave transmitted through the microstrip line type transmission line 16 and returned by reflection is measured. In this manner, determined is the delay time of the reflected wave, by the presence/absence of the object 112, as illustrated in FIG. 3.

Then the liquid reservoir 113 is washed with purified water, to remove the double-strand DNA. After drying, an aqueous solution of DNA, converted as single-strand for example by a heating, is dropped in the liquid reservoir 113 and is measured. In this manner determined again is the delay time of the reflected wave, by the presence/absence of the object 112, as illustrated in FIG. 3.

The delay time of the object 112 is different between the case of aqueous solution of double-strand DNA and the case of aqueous solution of single-strand DNA. This fact can be utilized for determining whether an unknown sample is single-strand or double-strand, by dropping the aqueous solution of DNA which is unknown whether it is single-strand or double-strand in the liquid reservoir 113, and by measuring the terahertz wave.

The present example has shown a construction in which the signal line 15, constituting the microstrip line type transmission line 16, is discontinued as the reflection unit 110. It is also possible to utilize, as described above, a construction in which the ground electrode 12 constituting the microstrip line type transmission line 16 is discontinued, or a construction in which the thickness of the dielectric layer 14 is changed discontinuously. Also a construction in which the width of the signal line 15 is changed discontinuously or a bend in the signal line 15 may be utilized as the reflection unit.

Second Example

Figure 5A:
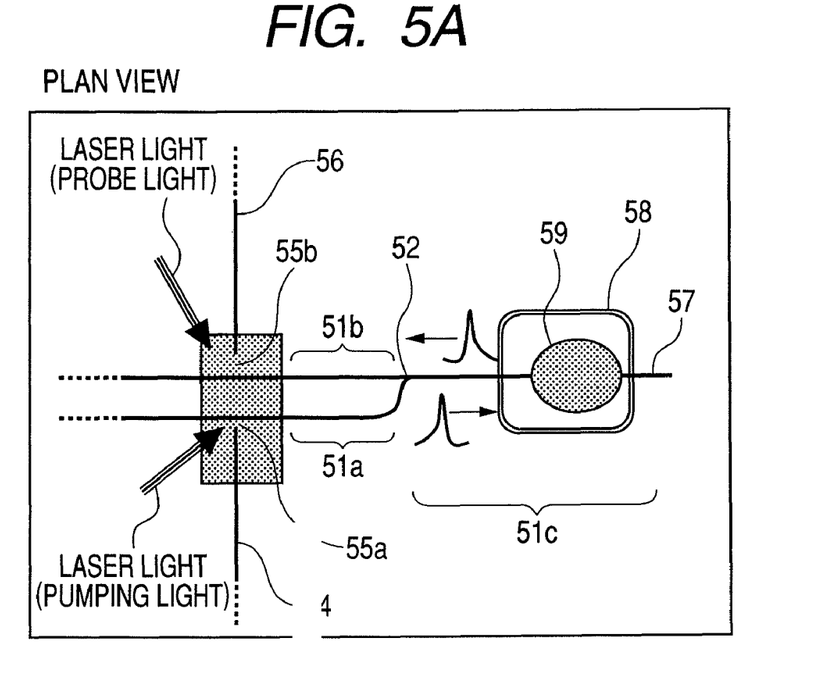
FIGS. 5A and 5B are schematic views illustrating an inspection apparatus of a second example of the present invention, having a branching point.
Figure 5B:
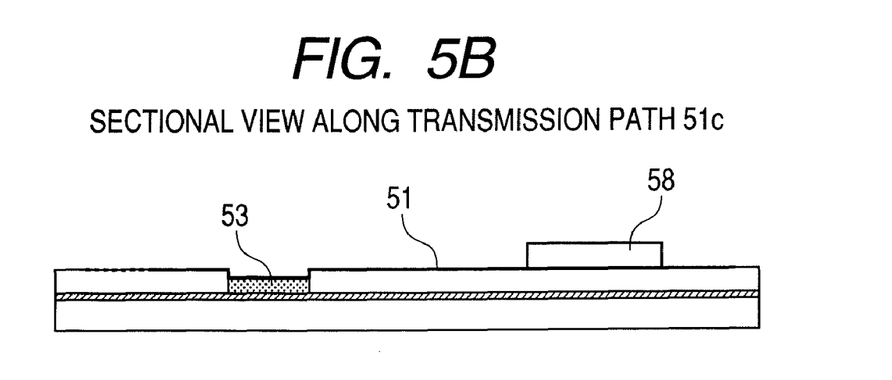

A second example of the present invention will be described with reference to FIGS. 5A and 5B. In the present example, a microstrip line type transmission line 51, constituted of a signal line, a dielectric member and a ground electrode, includes a branching point 52. In FIGS. 5A and 5B and with respect to the branching point 52, a transmission line extending to lower left side will be referred to as a microstrip line type transmission line 51a, a transmission line extending to upper left side will be referred to as a microstrip line type transmission line 51b, and a transmission line extending to right side will be referred to as a microstrip line type transmission line 51c.

At the branching point 52, two signal lines extend parallel over an appropriate coupling length, whereby the terahertz wave supplied to the transmission line 51a almost all passes through the branching point 52 and is coupled with the transmission line 51c toward the reflection unit 57, and the terahertz wave transmitting from the reflection unit 57 to the branching point 52 almost all passes through the branching point 52 and is coupled with the transmission line 51b toward the detecting unit.

On the low temperature-grown gallium arsenide film 53, the transmission line 51a and the bias supplying line 54 are disposed across a gap 55a. Also the transmission line 51b and the signal reading line 56 are disposed across a gap 55b, on the low temperature-grown gallium arsenide film 53. In the transmission line 51c, the signal line includes a discontinuity, which constitutes the reflection unit 57. In a region between the reflection unit 57 and the branching point 52, a liquid reservoir 58 is provided as the inspection unit. By dropping an object 59 in the liquid reservoir 58, the object of a trace amount can be measured with a high sensitivity.

In the present example, the object 59 and the terahertz wave executes interaction twice, in the forward path in which the terahertz wave supplied from the supplying unit of the electromagnetic wave supplying and detecting unit to the transmission line 51a is transmitted through the branching point 52 to the reflection unit 57, and in the returning path from the reflection unit 57 to the branching point 52. Therefore, it is possible not only to obtain the effect of the present invention of enabling a highly sensitive detection but also, as an effect specific to the present example, to increase the distance between the gap 55a and the gap 55b than in the first example, by the presence of the branching point 52. Thus obtained is an advantage that the irradiations of pumping light and probe light on the respective gaps is facilitated.

In general, when the areas irradiated by the pumping light and the probe light overlap with each other, large noises tend to be mixed in the signal. For this reason, it is desirable that these lights are so focused as not to overlap with each other. In the case that the distance between the gap 55a and the gap 55b is about 10 μm, it is desirable to form the light focusing points of a diameter of 10 μm or less for the pumping light and the probe light, so that an objective lens of a high N.A. is desirably used. On the other hand, in the case that the distance between the gap 55a and the gap 55b is as large as about 1 mm, a lens of a low N.A. may be used, whereby a simplification and a lower cost of the apparatus can be expected.

In the present example, since the distance between the gap 55a and the gap 55b can be increased owing to the presence of the branching point 52, the electromagnetic wave supplying and detecting unit as described in the foregoing embodiment and illustrated in FIG. 10 may be adopted easily.

Third Example

A third example of the present invention will be described with reference to FIGS. 6A and 6B. Also in the present example, as in the first example, a microstrip line type transmission line 61, an electromagnetic wave supplying and detecting unit 62, a reflection unit 63 and a liquid reservoir 64 for dropping an object are formed on the substrate. In the present example, on the signal line 65 constituting the microstrip line type transmission line 61, an antenna 66 is formed on a side opposite to the discontinued reflection unit 63. The antenna 66 of an inverted triangular shape is connected to the signal line 65, but an antenna of any shape, capable of suppressing the unnecessary reflected waves and radiating the transmitted electromagnetic wave into the air, may be utilized.

Also in the present example, a terahertz wave is generated by applying a voltage of about 10 V to a bias voltage supplying line 67 and irradiating a gap 68a with a pumping light, and is transmitted on the microstrip line type transmission line 61. In this state, the terahertz wave includes not only a component transmitting toward the reflection unit 63 but also a component transmitting to the opposite side. The terahertz wave transmitted to the opposite side is transmitted without reflection and is attenuated gradually, unless an impedance mismatch (for example a change in the thickness of the dielectric layer of the transmission line 61) inducing a reflection is present. However, in the case that an impedance mismatched position is present for example because of a condition in the production, the terahertz wave is reflected at such position and returns to the electromagnetic wave supplying and detecting unit 62. Also in the present example, as already illustrated in FIG. 4, the terahertz wave may be reflected at the boundary between the dielectric layer (BCB) and the low temperature-grown gallium arsenide film.

Figure 6A:
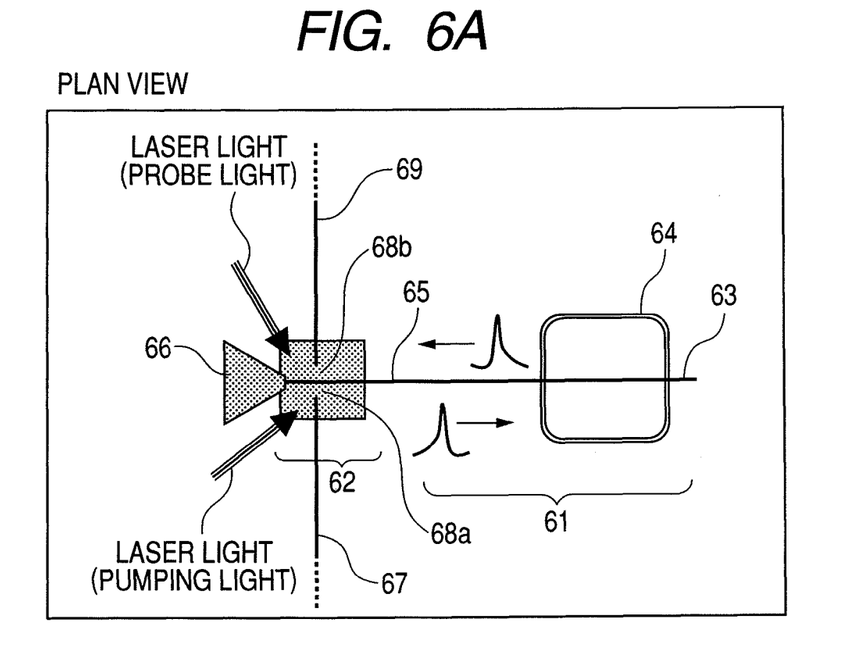
FIGS. 6A and 6B are schematic views illustrating an inspection apparatus of a third example of the present invention, having an antenna.
Figure 6B:
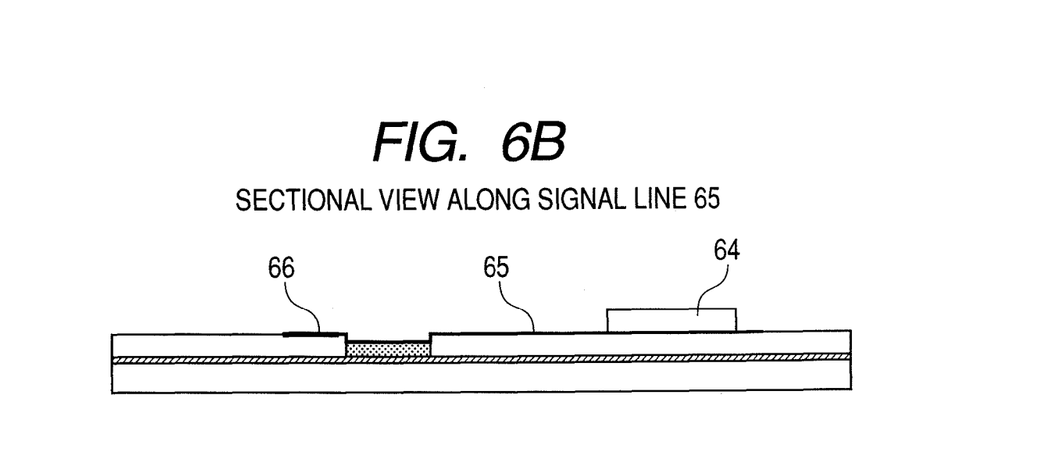

Therefore, the antenna 66 is disposed as illustrated in FIGS. 6A and 6B and the electromagnetic wave transmitted in the direction opposite to the reflection unit 63 is radiated into the air from the antenna 66, whereby the unnecessary reflected wave can be suppressed.

Figure 7:
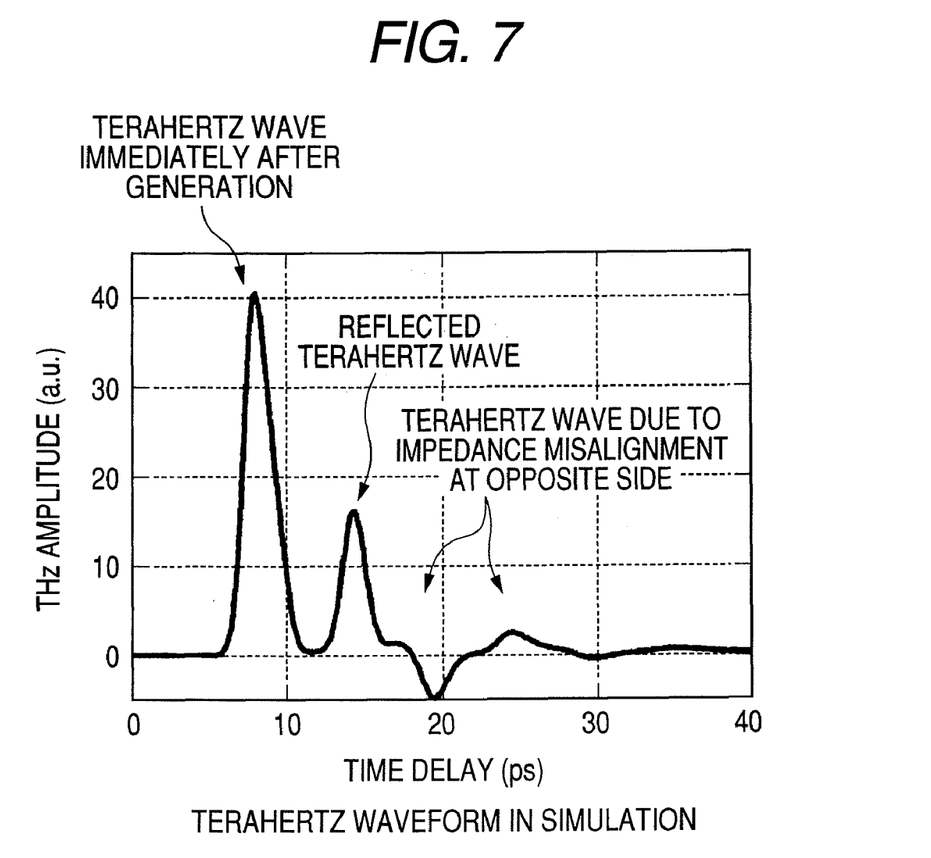
FIG. 7 is a schematic view illustrating a waveform of a terahertz wave as a function of time, in the inspection apparatus having an antenna, obtained by a simulation.

Instead of the antenna, a substance capable of absorbing the terahertz wave (for example a water-containing polymer) may be disposed at the terminal end of the transmission line 61 opposite to the reflection unit 63. As an example, considered is a case of disposing an antenna or a substance capable of absorbing the terahertz wave at such opposite terminal end thereby radiating or absorbing 100% of the terahertz wave transmitted to the opposite side. A waveform of the terahertz wave obtained in such case was determined by a simulation, and is shown in FIG. 7. It can be understood that the terahertz wave, derived from the impedance mismatch portions at the opposite terminal end, is suppressed.

Also in the present example, the terahertz wave is detected by a signal reading line 69, connected to the signal amplifier, by irradiating a gap 68b of the electromagnetic wave supplying and detecting unit 62 with an ultra short pulsed laser light. The present example provides an effect of removing and suppressing the reflected terahertz wave that does not contribute to the inspection of the object.

Fourth Example

Figure 8A:
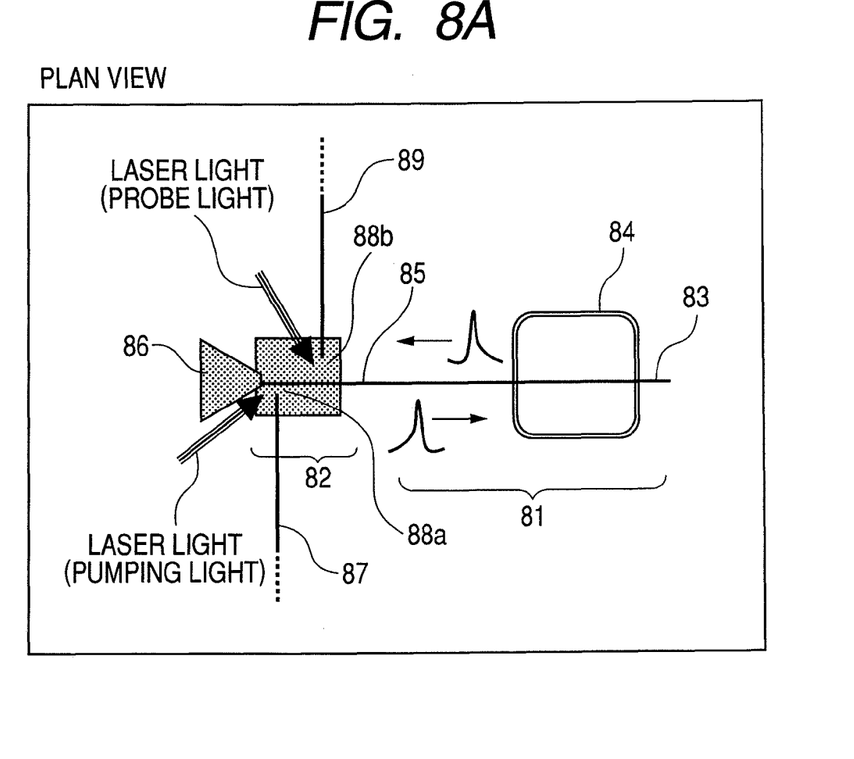
FIGS. 8A and 8B are schematic views illustrating an inspection apparatus of a fourth example of the present invention.
Figure 8B:
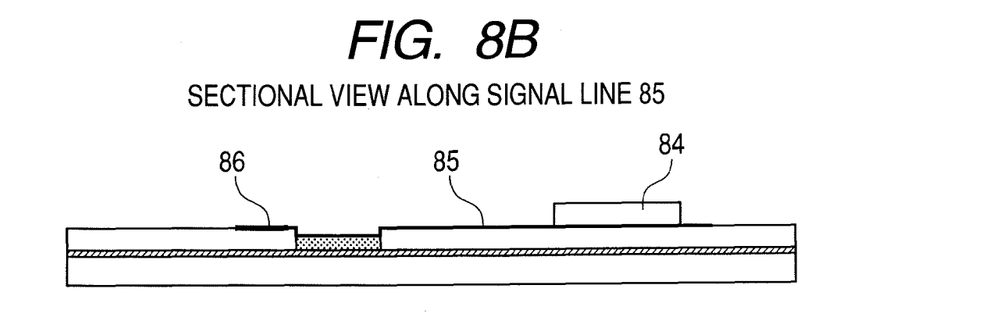

A fourth example of the present invention will be described with reference to FIGS. 8A and 8B. Also in the present example, as in the third example, a microstrip line type transmission line 81, an electromagnetic wave supplying and detecting unit 82, a reflection unit 83 and a liquid reservoir 84 for dropping an object are formed on the substrate. Also on the signal line 85 constituting the transmission line 81, an antenna 86 is formed on a terminal end opposite to the discontinued reflection unit 83.

In the present example, a bias voltage supplying line 87 and a signal reading line 89 are disposed across respective gaps 88a and 88b to the signal line 85. The bias voltage supplying line 87 and the signal reading line 89 are not arranged linearly but are disposed with a distance of about from 100 μm to 1 mm therebetween, perpendicularly to the signal line 85.

By positioning the bias voltage supplying line 87 and the signal reading line 89, not on a line but with a distance therebetween, it is facilitated to focus the pumping light and the probe light in separate manner. Therefore obtained is an effect similar to that in the construction described in the second example.

Fifth Example

Figure 9A:
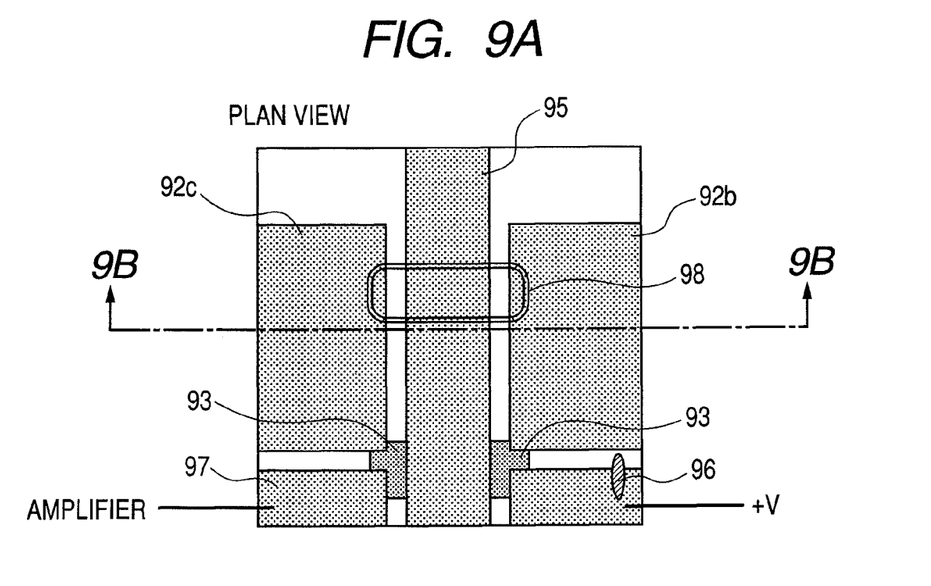
FIGS. 9A and 9B are schematic views illustrating an inspection apparatus of a fifth example of the present invention, utilizing a transmission line of a coplanar waveguide type with a ground.
Figure 9B:
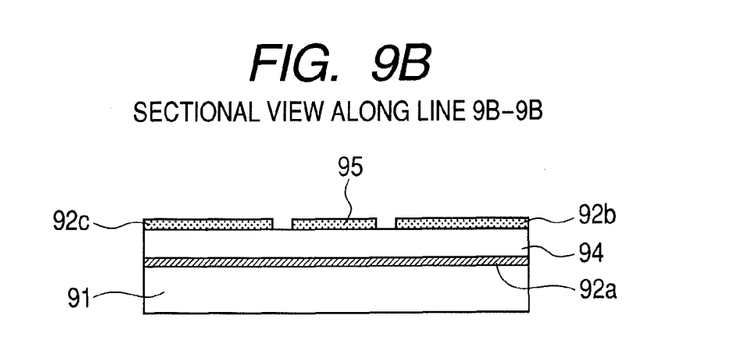

A fifth example of the present invention will be described with reference to FIGS. 9A and 9B. In the present example, a ground electrode 92a is formed on a substrate 91 for example of silicon, by an evaporation process or the like. Also a low temperature-grown gallium arsenide film 93 is formed, for example by an epitaxial lift-off process, on the ground electrode 92a. Also a dielectric layer 94 (for example BCB) is formed for example by a spin coating method. A part of the dielectric layer 94 is removed for example by a dry etching to expose the low temperature-grown gallium arsenide film 93.

Also a signal line 95, ground electrodes 92b, 92c, a bias voltage supplying line 96 and a signal reading line 97 are formed for example by an evaporation process. Also a liquid reservoir 98 is formed with a resinous material, so as to lie over the signal line 95 and the ground electrodes 92a, 92b.

The transmission line constituted of the ground electrodes 92a, 92b, 93c, the dielectric layer 94, and the signal line 95 is so-called grounded coplanar waveguide type transmission line. The ground electrodes 92b, 92c are discontinuous on the way, thereby constituting reflection units. Also a bias voltage supplying line 96, a low temperature-grown gallium arsenide film 93, a signal line 95 and a signal reading line 97 constitutes the electromagnetic wave supplying and detecting unit for the terahertz wave.

In the above-described construction, a terahertz wave is generated by applying a voltage of about 10 V to the bias voltage supplying line 96 and by focusing a femtosecond laser light in the low temperature-grown gallium arsenide film 93 in an area positioned between the bias voltage supplying line 96 and the signal line 95. The generated terahertz wave is transmitted through the grounded coplanar waveguide type transmission line and executes an interaction with the object placed in the liquid reservoir 98. The terahertz wave reflected in the reflection unit constituted of the discontinuity of the ground electrode again executes an interaction with the object and is then detected by the signal reading line 97. The information of the object can be detected, as in the foregoing examples, from a change in the transmission state of the terahertz wave.

The grounded coplanar waveguide type transmission line of the present example is capable of transmitting the electromagnetic wave of a lower frequency (for example of about 100 GHz) more easily in comparison with the microstrip line type transmission line. Therefore, the present example has an advantage of being suitable to the object inspection with an electromagnetic wave of a lower frequency.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2007-063613, filed Mar. 13, 2007, which is hereby incorporated by reference herein in its entirety.

What is claimed is:

1. An apparatus for inspecting an object based on a change in an electromagnetic wave transmission state caused by plural times of interactions between an electromagnetic wave and the object, comprising:
   a transmission line;
   an electromagnetic wave supplying and detecting unit for supplying and detecting the electromagnetic wave;
   a reflection unit for reflecting the electromagnetic wave as the electromagnetic wave is transmitted through the transmission line; and
   an inspection unit for placing the object between the electromagnetic wave supplying and detecting unit and the reflection unit, wherein
   the transmission line, the electromagnetic wave supplying and detecting unit, the reflection unit, and the inspection unit are formed on a same substrate,
   the electromagnetic wave supplying and detecting unit includes a supplying unit for supplying the electromagnetic wave and a detecting unit for detecting the electromagnetic wave, and
   the supplying unit and the detecting unit are formed adjacent to each other to include a continuous and common same-layered structure.

2. The apparatus according to claim 1, wherein the transmission line includes a branch, the inspection unit is arranged between the branch and the reflection unit, the electromagnetic wave supplied from the electromagnetic wave supplying and detecting unit is coupled with the transmission line passing through the branch to the reflection unit, and the electromagnetic wave directed from the reflection unit to the branch is coupled with the transmission line passing through the branch to the electromagnetic wave supplying and detecting unit.

3. The apparatus according to claim 1, wherein the transmission line includes a dielectric unit and an electroconductive unit disposed at one or more portions of the dielectric unit.

4. The apparatus according to claim 1, wherein the reflection unit discontinuously changes an impedance of the transmission line.

5. The apparatus according to claim 1, wherein the electromagnetic wave has a frequency in a range of 30 GHz-30 THz.

6. The apparatus according to claim 1, wherein the continuous and common same-layered structure includes a low-temperature-grown gallium arsenide.

* * * * *